United States Patent [19]

Ducos et al.

[11] 4,184,879
[45] Jan. 22, 1980

[54] ENDODONTICAL TREATMENT PASTE

[75] Inventors: Jacques Ducos; Jean-Pierre Duprez, both of Lyons, France

[73] Assignee: Laboratoire Spad, Quetigny, France

[21] Appl. No.: 891,040

[22] Filed: Mar. 28, 1978

[30] Foreign Application Priority Data

Apr. 20, 1977 [FR] France ............................ 77 12649

[51] Int. Cl.² .............................................. C09K 3/00
[52] U.S. Cl. .................................... 106/35; 433/228; 424/332
[58] Field of Search ...................... 106/35; 424/332; 260/588; 32/15

[56] References Cited

U.S. PATENT DOCUMENTS

| 987,451 | 3/1911 | Eilertsen | 106/35 |
| 1,900,237 | 3/1933 | Harshman | 106/35 |
| 2,516,438 | 7/1950 | Wheeler | 106/35 |

Primary Examiner—Lorenzo B. Hayes
Attorney, Agent, or Firm—Gerald J. Ferguson, Jr.; Joseph J. Baker

[57] ABSTRACT

An endodontical treatment paste, in particular for the root canal filling of teeth comprising a non-coagulating antiseptic agent such as parachlorophenol camphor, a mixture of products for causing the setting of the paste such as a mixture of eugenol and zinc oxide, and an agent for retarding the setting of the paste such as diiodothymol. The paste may also include pulverized menthol crystals and/or silver powder.

7 Claims, 1 Drawing Figure

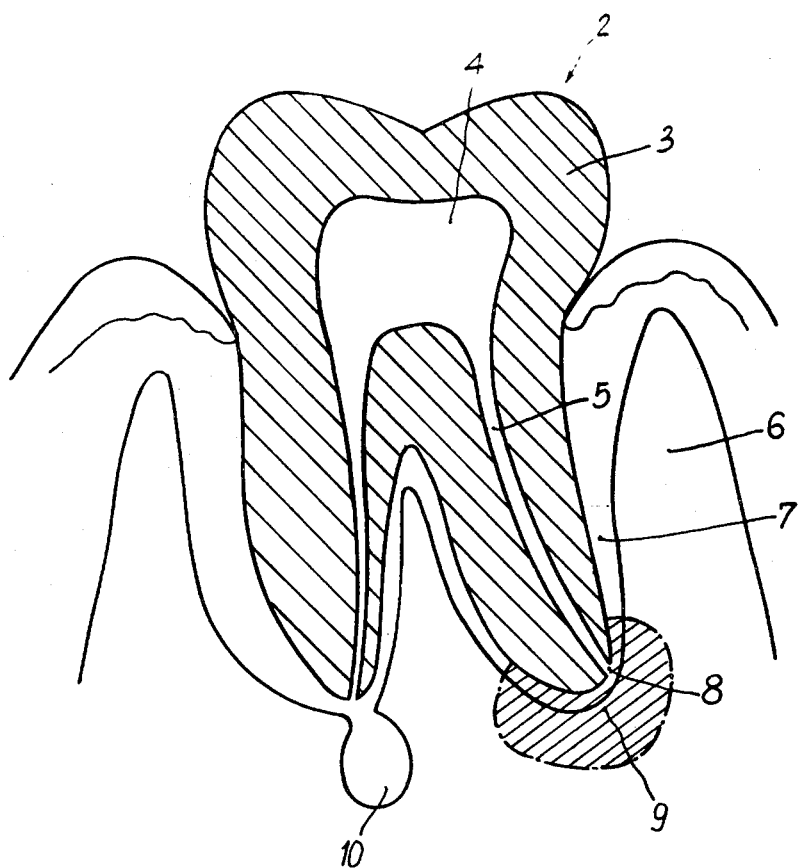

ENDODONTICAL TREATMENT PASTE

BACKGROUND OF THE INVENTION

The invention relates to an endodontic treatment paste for the root canal filling of teeth, which may or may not be infected and of which the periapical area may or may not be affected. The invention also relates to a process for the preparation of this paste.

DISCUSSION OF THE PRIOR ART

Several pastes are already known on the market for filling root canals, particularly Walkhoff's paste. Walkhoff's paste essentially contains parachlorophenol camphor, which is an antiseptic agent whose essential purpose is to dissolve albumins and which can therefore progressively penetrate into the canaliculi of the tooth. However, Walkhoff's paste has a major disadvantage which arises from its total resorption, which occurs both in the periapical area and in the canal area of the tooth. This resorption is due to its physicochemical instability. From a practical point of view it has been shown that even in the most favourable cases, there is no longer any trace of paste in the previously filled canals, one year after filling of the canals has taken place.

This resorption gives rise to the risk of possible reinfection and prevents any prosthetic restoration of the tooth.

Maisto's paste is another known product for filling of root canals. This paste includes as ingredients parachlorophenol camphor, zinc oxide, lanolin, and iodoform. Because of the presence of zinc oxide, this paste is resorbed more slowly, but in the long term is no more effective than Walkhoff's paste.

Hydrocortisone pastes are also available. Hydrocortisone leads to an inhibition of the inflammatory granuloma. The absence of polynuclear stimulation prevents the development of immunological response. As a result, an acute state then develops into a chronic lesion.

A certain number of so-called "conventional" pastes are also known, which set rapidly, within about two hours. Once the paste has hardened the process of disinfection is halted. These pastes therefore have the disadvantage of bringing the disinfection phase to an end too quickly. Before the canal filling operation (obturation) is performed repeated antiseptic dressings must be applied. Such dressings because of their slightly caustic or irritating nature can be harmful to the periapical tissues.

SUMMARY OF THE INVENTION

An object of the present invention is to provide an endodontical treatment paste which has high antiseptic power but is not resorbed in the root canals. Thus, it is an object of the invention to provide a mixture which, while permitting slow diffusion of antiseptic products, completely hardens within a period which may be as long as six months from the time when the filling is made.

Experience has in fact shown that an endodontical treatment paste must remain active for a long time, because proliferation of residual bacteria occurs as soon as the action of the antiseptic decreases, that is to say as soon as the paste hardens. This emphasises the importance of the antiseptic function of filling materials in the healing of the periapical tissues.

DETAILED DESCRIPTION

According to the invention there is provided an endodontical treatment paste, in particular for the root canal filling of teeth, comprising a non-coagulating antiseptic agent, a mixture of products for causing the paste to set, and an agent for retarding the setting of the paste thereby to reduce the ultimate hardness of the paste.

Preferably, the antiseptic agent is parachlorophenol camphor; the products which will cause the paste to set are eugenol and zinc oxide, and the agent for retarding the setting of the setting products is diiodothymol.

Parachlorophenol camphor possesses all the antiseptic properties of parachlorophenol, but does not have the coagulating power of parachlorophenol. Non-coagulation is an essential characteristic of the antiseptic agent of the present invention. Camphor reduces the surface tension of the product and provides a liquid having a good wetting action and capable of adhering well to the canal walls. Furthermore, parachlorophenol camphor lengthens the setting time of the paste and progressively diffuses into the seocndary canaliculi.

Eugenol is the active principle of oil of cloves. Its affinity for zinc oxide gives rise to the setting of the paste. With regard to zinc oxide, it should be noted that this is a non-irritating vehicle.

Diiodothymol is a non-irritating antiseptic which provides the paste with fluidity and enables the paste to pass more easily into the canals of the tooth. It is helpful because it retards the setting of the paste and reduces the ultimate hardness of the paste.

Moreover, should the paste happen to be forced into the periapical area, the progressive solubilisation of diiodothymol brings about the break down of the excess paste.

The paste of the invention may additionally contain pulverised menthol crystals. These crystals combine great antiseptic power with low irritating effect on tissues with which it comes into contact. Furthermore, such crystals are not volatile and have a vasoconstrictive and analgesic function.

The paste of the invention may also contain silver powder, which increases the radio-opacity of the paste and in addition has the advantage of being bacteriostatic.

In order to prepare the paste of the invention, a first mixture is on the one hand prepared which is in liquid form and comprises 15 to 25% of parachlorophenol camphor and 75 to 85% of eugenol, together with from 2 to 8% of pulverised menthol crystals (parts by weight).

A second mixture is also prepared, which is in the form of a powder and which comprises (by weight) 69 to 80% of zinc oxide, 17 to 25% of diiodothymol, and 1 to 2% of silver powder.

The paste is prepared by the user immediately before the paste is to be used. The paste is obtained by intimately combining the first liquid mixture and the second pulverulent mixture in a weight ratio of one part of liquid to 2.3 parts of powder.

Although silver powder is useful in facilitating X-ray observation of the teeth treated, its use is not indispensable in achieving satisfactory, durable filling of tooth canals; the same applies to the addition of menthol crystals, the analgesic effect of which is not always necessary. Consequently, in its simplest aspect the paste of the invention has the following composition (by weight) after combining the first and second mixtures:

parachlorophenol camphor: 4 to 8% approx.
eugenol: 24 to 22% approx.
zinc oxide: 48 to 58% approx.
diiodothymol: 12 to 18% approx.

When this paste contains menthol crystals and silver powder, minimum quantities of these additives are used, so that the basic composition given above is scarcely modified. In a paste containing them, these two products are added in the following proportions (by weight):

pulverised menthol crystals: 1.40 to 2.90% approx.
silver powder: 0.70 to 1.45% approx.

In practice a paste giving full satisfaction is obtained by using the different substances indicated in proportions close to the mean value of the limit percentages mentioned above.

After being placed in position in a root canal, within about six to eight days the paste of the invention acquires the consistency of a mastic and maximum hardening is achieved after six to eight months. Redrilling of the canals or their partial deobturation for prosthetic purposes is possible two weeks after the making of the canal filling, the consistency of the paste after this time being such as to permit this operation to be performed.

Because of its antiseptic properties the paste of the invention is useful above all for the root canal filling of infected teeth. However, it may also be used in cases of pulpotomy after pulpitis, or pulpotomy for prosthetic purposes.

The use of the paste of the invention will now be explained for convenience with reference to the accompanying drawing showing a sectional view of a tooth.

Referring to the drawing, the tooth 2 comprises a crown 3, a pulp chamber 4 from which extend canals 5 ending at the apex 8 at a region known as the periapical area 9. The tooth 2 sits in the alveolar bone 6 and is surrounded by ligaments 7. The reference numeral 10 indicates a cyst, the X-ray image of which is shown diagrammatically.

When a tooth is not infected, the canals are drilled and then filled without any attempt being made to go beyond the apex 8.

In general, when a tooth has an apical lesion which can be detected by X-rays, such as the cyst 10, and when pain is felt, after the canals 5 of the tooth have been drilled during a first session of dental treatment, a plug of cotton wool lightly impregnated with parachlorophenol camphor in an occlusive dressing is inserted into the pulp chamber and left in place for from four to ten days. Subsequently at a second session of dental treatment the root filling is made, extending beyond the apex to an extent depending upon the size of the lesion.

If the patient feels no pain, the root filling can be performed during the said first session of the dental treatment, the root filling extending beyond the apex 8 to an extent depending upon the size of the lesion.

In cases of necrobiosis (pulp death) the root filling is made during the first session of dental treatment. If there is a purulent discharge, the lesion should be allowed to drain before the filling is made.

DESCRIPTION OF PREFERRED EMBODIMENTS

The following Example illustrates the present invention.

EXAMPLE

The tables given below show the results obtained in a certain number of clinical cases using an endodontical treatment paste in accordance with the invention.

Table I corresponds to a study relating to 1,171 cases treated, including 571 infected teeth without a periapical focus and 600 uninfected teeth.

Table II corresponds to a study relating to 549 cases of infected teeth with a diffuse focus.

Table III corresponds to a study relating to 280 cases of infected teeth having a circumscribed focus.

Table IV shows an analysis of the results of Tables I to III.

In the Tables where two figures corresponding to one and the same type of tooth are shown one above the other, the first figure corresponds to the number of teeth treated which belong to the upper jaw and the second figure corresponds to the number of teeth treated which belong to the lower jaw.

The following characteristics were applied as criteria of positive results:

elimination of pain symptoms;
absence of tooth mobility;
reduction of focus of infection and of X-ray image, with osseous retrabeculation (bony regeneration);
diminution of the pathological ligamentary space.

A study of the results shown in Tables I to IV below shows that the paste of the invention brings about a great improvement over the existing technique. It is believed that the improvement results from the paste of the invention having a durable antiseptic action resulting from its extremely slow setting time. In addition, the paste of the invention has the following properties:

ease of introduction;
filling of the apex of the tooth and clogging of the canaliculi of the tooth;
adherence to the walls of the canals;
physically unchanging preservation in the canal;
chemically unchanging preservation in the canal;
radio-opacity;
no danger to the periapical area;
easily removed if necessary.

Furthermore, the paste of the invention permits a considerable saving of time in the treatment. By use of the present paste it is possible to treat a tooth in a single session whereas if other known methods were applied such treatment would have required a number of sessions (for which reason extraction of the tooth is often preferred to canal filling of the tooth).

In addition, when prosthetic or non-prosthetic reconstitution of crowns is required, such reconstitution can be performed after two weeks.

For the execution of the clinical tests mentioned above, use was made of a paste prepared at the moment of use by intimately combining one part of a first liquid mixture of the following composition:

parachlorophenol camphor: 20%
eugenol: 80% and 2.5 parts of a second pulverulent mixture of the following composition:

zinc oxide: 75%
diiodothymol: 21%
menthol crystals: 2.5%
silver powder: 1.5%

It will be observed that the above composition of the basic mixtures differs from that previously given above in the sense that the pulverised menthol crystals form part of the second mixture instead of being part of the first mixture.

However, the paste finally obtained is the same. In fact, the menthol crystals may be incorporated in the second mixture provided that during operation the necessary precautions are taken to avoid any localised heating. The menthol crystals must in fact be incorporated in the form of a very fine powder having a grain size of a few microns. Satisfactory intimate mixing of this powder with the other pulverulent substances is achieved by grinding them together. Any heating of the menthol, even localised heating, gives rise to recrystallisation in a coarser form.

Consequently, in order to avoid this difficulty in a simple manner, it is preferable to incorporate the pulverised menthol crystals in the first mixture which contains only liquids (parachlorophenol camphor and eugenol). Homogeneity is achieved without the risk of heating. The small amount of powdered menthol does not change the liquid nature of this mixture.

Having regard to the above, for the easy industrial exploitation of the invention the preferred composition of the two mixtures is as follows:

First liquid mixture:
parachlorophenol camphor: 19% approx.
eugenol: 76.3% approx.
pulverised menthol crystals: 4.7% approx.
Second pulverulent mixture:
zinc oxide: 76.5% approx.
diiodothymol: 22.5% approx.
silver powder: 1% approx.

At the time of use one part by weight of the first mixture is intimately combined with 2.3 parts by weight of the second mixture. The figure of 2.3 units instead of 2.5 in the example of the paste for clinical tests takes into account the change made to the composition of the mixtures by transferring the menthol crystals from the second to the first mixture.

The foregoing clearly shows that the examples of composition given here may undergo modifications which are only equivalents not going beyond the scope of the invention.

Table I

| Type of teeth | Gross examined | Positive results | No arthritis | Slight arthritis | Severe arthritis | Imperfect results or failures |
|---|---|---|---|---|---|---|
| Incisors | 162 | 162 | 140 | 22 | 0 | 0 |
|  | 80 | 80 | 69 | 10 | 1 | 0 |
| Canines | 78 | 78 | 64 | 12 | 2 | 0 |
|  | 56 | 56 | 55 | 1 | 0 | 0 |
| Pre- | 180 | 180 | 117 | 40 | 23 | 0 |
| molars | 136 | 136 | 121 | 15 | 0 | 0 |
| Molars | 211 | 211 | 148 | 23 | 40 | 0 |
|  | 268 | 268 | 157 | 62 | 49 | 0 |

Table II

| Type of teeth | Cases examined | Positive results | No arthritis | Slight arthritis | Severe arthritis | Imperfect results or failures |
|---|---|---|---|---|---|---|
|  | 75 | 72 | 51 | 13 | 8 |  |

Table III

| Type of teeth | Cases examined | Positive results | No arthritis | Slight arthritis | Severe arthritis | Imperfect results or failures |
|---|---|---|---|---|---|---|
| Incisors | 42 | 40 | 21 | 12 | 7 | 3 |
|  | 23 | 22 | 12 | 6 | 4 |  |
| Canines | 11 | 11 | 7 | 3 | 1 | 0 |
|  | 9 | 9 | 7 | 0 | 2 |  |
| Pre- | 62 | 60 | 21 | 20 | 19 | 7 |
| molars | 37 | 32 | 13 | 12 | 7 |  |
| Molars | 26 | 24 | 11 | 10 | 3 | 5 |
|  | 40 | 37 | 19 | 7 | 11 |  |

Table IV

| Classification | | Cases | Positive results | % |
|---|---|---|---|---|
| Non-infected teeth | | 600 | 600 | 100 |
| Infected teeth | without focus | 571 | 571 | 100 |
|  | with diffuse focus | 549 | 524 | 95.44 |
|  | circumscribed focus | 280 | 265 | 94.64 |

What is claimed is:

1. An endodontical treatment paste, in particular for the root canal filling of teeth, comprising parachlorophenol camphor as a non-coagulating antiseptic agent, a mixture of zinc oxide and eugenol for causing the paste to set, and di-iodothymol for retarding the setting of the paste to thereby reduce the ultimate hardness of the paste.

2. A paste according to claim 1, wherein the paste comprises, in proportions by weight:
   parachlorophenol camphor: from 4 to 8% approx.
   eugenol: from 24 to 22% approx.
   zinc oxide: from 48 to 58% approx.
   diiodothymol: from 12 to 18% approx.

3. A paste according to claim 1, additionally including pulverized menthol crystals which function as an analgesic and as a vasoconstrictor.

4. A paste according to claim 1, additionally including silver powder which will increase the radio-opacity of the paste.

5. A paste according to claim 4, wherein the paste includes, in proportions by weight:
   pulverised menthol crystals: from 1.40 to 2.90 approx.
   silver powder: from 0.70 to 1.45 approx.

6. A paste according to claim 4, wherein the paste is derived from a first composition comprising (in parts by weight):
   parachlorophenol camphor: 15 to 25%
   eugenol: 75 to 85%
   pulverised menthol crystals: 2 to 8%
and a second composition comprising (in parts by weight):
   zinc oxide: 65 to 80%
   diiodothymol: 17 to 25%
   silver powder: 1 to 2%,
the first and second compositions being separate entities and being intimately combined to form the paste before the paste is to be used, the first and second compositions being combined in amounts such that the weight ratio of the first composition to the second composition is 1:2.3.

7. A paste according to claim 6, wherein the first mixture comprises, by weight:
   approx. 19% of parachlorophenol camphor
   approx. 76.3% of eugenol and
   approx. 4.7% of pulverised menthol crystals,
and the second mixture comprises, by weight:
   approx. 76.5% of zinc oxide
   approx. 22.5% of diiodothymol and
   approx. 1% of silver powder.

* * * * *